(12) United States Patent
Pressman et al.

(10) Patent No.: US 7,495,113 B2
(45) Date of Patent: *Feb. 24, 2009

(54) METHOD OF PURIFYING DIANHYDRIDES

(75) Inventors: Eric James Pressman, East Greenbush, NY (US); Lioba Maria Kloppenburg, Mt. Vernon, IN (US); John Morgan Whitney, Niskayuna, NY (US); Abhijit Namjoshi, Guilderland, NY (US); Spencer Thomas Oulman, Texas City, TX (US)

(73) Assignee: SABIC Innovative Plastics, Pittsfield, MA (US)

( * ) Notice: Subject to any disclaimer, the term of this patent is extended or adjusted under 35 U.S.C. 154(b) by 545 days.

This patent is subject to a terminal disclaimer.

(21) Appl. No.: 11/022,905

(22) Filed: Dec. 22, 2004

(65) Prior Publication Data

US 2006/0135791 A1    Jun. 22, 2006

(51) Int. Cl.
*C07D 493/00* (2006.01)
(52) U.S. Cl. ..................................................... 549/239
(58) Field of Classification Search ................ 549/236, 549/239, 241, 247
See application file for complete search history.

(56) References Cited

U.S. PATENT DOCUMENTS

| | | | |
|---|---|---|---|
| 1,301,388 A | 4/1919 | Courtney et al. | |
| 2,786,805 A | 3/1957 | Sullivan et al. | |
| 2,937,189 A | 5/1960 | Walter et al. | |
| 2,985,665 A | 5/1961 | Lawn et al. | |
| 3,236,885 A | 2/1966 | Gray | |
| 3,338,923 A | 8/1967 | Peterlein | |
| 3,880,890 A | 4/1975 | Fabian | |
| 4,870,194 A | 9/1989 | Molinaro et al. | 549/241 |
| 4,906,760 A | 3/1990 | Mueller et al. | 549/239 |
| 4,914,231 A | 4/1990 | Manami et al. | 562/429 |
| 5,145,971 A * | 9/1992 | Lesins | 549/250 |
| 5,336,788 A | 8/1994 | Lesins | 549/250 |

FOREIGN PATENT DOCUMENTS

| | | |
|---|---|---|
| EP | 0 421 046 | 4/1991 |
| EP | 0 538 547 | 4/1991 |
| GB | 0 823 507 | 11/1959 |

OTHER PUBLICATIONS

European Search Report dated Mar. 24, 2006.

* cited by examiner

*Primary Examiner*—D. Margaret Seaman
*Assistant Examiner*—Nizal S Chandrakumar

(57) ABSTRACT

A method of preparing a purified dianhydride is provided where said method comprises the steps of preparing a first mixture comprising water, at least one inorganic acid, and at least one dianhydride, said dianhydride comprising at least one impurity which is soluble in aqueous acid heating said first mixture until substantially all of said dianhydride is converted to a tetraacid comprised in a second mixture; filtering at least a portion of said second mixture to provide a solid tetraacid and a filtrate, said filtrate comprising at least a portion of said impurity; and heating the tetraacid provided in a solvent with concurrent distillation of water to provide a third mixture comprising a purified dianhydride and a solvent.

21 Claims, No Drawings

METHOD OF PURIFYING DIANHYDRIDES

BACKGROUND OF THE INVENTION

This invention relates to a method for preparing a purified dianhydride. More particularly, the method relates to preparing a purified oxydiphthalic anhydride.

Dianhydrides are often prepared from their chloro derivatives of corresponding anhydride by coupling two molecules of the chloro anhydride, generally through use of an additional coupling reagent. The crude product of such a coupling reaction often includes organic solvents, unreacted starting material(s) and catalysts, ionic substances, and various colored materials of unknown composition.

Various processes of the purification of phthalic anhydride and pyromellitic acid via activated carbon are disclosed in U.S. Pat. Nos. 1,301,388; 2,937,189; 2,985,665; 3,236,885; and 3,236,885. U.S. Pat. No. 2,786,805 teaches that phthalic anhydride can be purified by slurrying the material in water, heating the slurry to 375-400 F, removing the anhydride by passing steam into the mixture and condensing the purified phthalic anhydride vapors. While U.S. Pat. No. 3,338,923 discloses a method of purifying pyromellitic dianhydride by treatment with ketones. Furthermore, it discloses that the material can be purified by converting the dianhydride into the acid with water and recrystallizing the acid from water in the presence of activated carbon. In U.S. Pat. No. 4,870,194, oxydiphthalic anhydride can be purified by filtering or centrifuging a hot solution of the material in a high boiling solvent to remove impurities, followed by cooling the solution to precipitate the oxydiphthalic anhydride, which then can be isolated from the solution by filtration or centrifugation.

U.S. Pat. No. 4,906,760 discloses that metal ion impurities may be removed from aromatic anhydrides by refluxing the material in an aqueous solution, clarify the solution with activated carbon, filtering off the carbon, cooling and crystallizing the purified aromatic acid. U.S. Pat. No. 4,906,760 discloses that metal ion impurities may be removed from aromatic anhydrides "by refluxing the anhydride in an aqueous solution, provide an activated adsorption agent such as activated carbon to clarify the solution, filtering off the absorption agent (and recovering the polyacid therefrom by washing the filter cake with warm water for return to the main solution), allowing the solution to stand and cool and precipitate the purified polyacid.

A British Patent, #823,507, discloses that tetrachlorophthalic acid can be purified by dissolving it in water containing 2-20% of a water miscible ether. The crude tetrachlorophthalic anhydride is dissolved in a mixture of water and the ether and then filtered hot.

U.S. Pat. No. 4,914,231 discloses a method for purifying diphenylsulfone tetracarboxylic acids by dissolution in a mixture of water and acetic acid to generate the crude tetracarboxylic acid and allowing the acid to crystallize. When the crude diphenylsulfone tetracarboxylic acid contains heavy metal ions, removal of the ions is more effective if the solution is treated with cation exchange resin, or with oxalic acid prior to crystallization. European Pat. No. 0421 046 A1 discloses a process for producing highly pure 3,3',4,4'-biphenyltetracarboxylic acid or its respective anhydride. The anhydride is treated with hot water at a temperature of 95 to 105° C. The impurities dissolve in the water and the anhydride is converted to the acid.

U.S. Pat. No. 5,145,971 discloses a process for the preparation of purified oxydiphthalic acid from impure oxydiphthalic anhydride, by treating with a mixture of water and propionic acid or butyric acid to produce oxydiphthalic acid. The acid may be treated to reform oxydiphthalic anhydride.

The method for generating oxydiphthalic anhydride from oxydiphthalic acid has been disclosed in U.S. Pat. No. 5,336,788 where the acid is mixed with an organic solvent, followed by addition of propionic acid and co-distillation of the acid with water, and heating the resulting slurry to the boiling point of the slurry to remove any water.

However there is a continuing need to develop an improved process to isolate and purify the dianhydrides so as to remove the impurities such as those salt-by product, residual catalyst and some residual reactants that tend to contaminate the dianhydride. It would be desirable therefore to provide such a method for preparing a purified dianhydride devoid of contaminations.

BRIEF SUMMARY OF THE INVENTION

In one aspect, the present invention provides a method of preparing a purified dianhydride, said method comprising, (a) preparing a first mixture comprising water, at least one inorganic acid, and at least one dianhydride, said dianhydride;

(b) heating said first mixture until substantially all of said dianhydride is converted to a tetraacid comprised in a second mixture;

(c) filtering at least a portion of said second mixture to provide a solid tetraacid and a filtrate, said filtrate comprising; and (d) heating the tetraacid provided by step (c) in a solvent with concurrent distillation of water to provide a third mixture comprising a purified dianhydride and a solvent.

In another aspect, the present invention relates to a method of preparing a purified oxydiphthalic anhydride.

DETAILED DESCRIPTION OF THE INVENTION

The present invention may be understood more readily by reference to the following detailed description of preferred embodiments of the invention and the examples included herein. In this specification and in the claims which follow, reference will be made to a number of terms which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "polymeric species" includes both polymeric and oligomeric materials. Polymeric materials are defined as having weight average molecular weights, $M_w$, greater than 15,000 daltons, and oligomeric materials are defined as having weight average molecular weights, $M_w$, less than 15,000 daltons.

As used herein the term "aliphatic radical" refers to an organic radical having a valence of at least one comprising a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl; difluorovinylidene; trichloromethyl, bromodichloromethyl, bromoethyl, 2-bromotrimethylene (e.g. —$CH_2CHBrCH_2$—), and the like. Further examples of aliphatic radicals include allyl, aminocarbonyl (i.e. —$CONH_2$), carbonyl, dicyanoisopropylidene (i.e. —$CH_2C(CN)_2CH_2$—), methyl (i.e. —$CH_3$), methylene (i.e. —$CH_2$—), ethyl, ethylene, formyl (i.e. —CHO), hexyl, hexamethylene, hydroxymethyl (i.e. —$CH_2OH$), mercaptomethyl (i.e. —$CH_2SH$), methylthio (i.e. —$SCH_3$), methylthiomethyl (i.e. —$CH_2SCH_3$), methoxy, methoxycarbonyl (i.e. $CH_3OCO$—), nitromethyl (i.e. —$CH_2NO_2$), thiocarbonyl, trimethylsilyl (i.e. $(CH_3)_3Si$—), t-butyldimethylsilyl, trimethyoxysilypropyl (i.e. $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e. $CH_3$—) is an example of a $C_1$ aliphatic radical. A decyl group (i.e. $CH_3(CH2)_{10}$—) is an example of a $C_{10}$ aliphatic radical.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as trifluoromethylphenyl, hexafluoroisopropylidenebis(4-phen-1-yloxy) (i.e. —$OPhC(CF_3)_2PhO$—), chloromethylphenyl; 3-trifluorovinyl-2-thienyl; 3-trichloromethylphen-1-yl (i.e. 3-$CCl_3Ph$-), 4(3-bromoprop-1-yl)phen-1-yl (i.e. $BrCH_2CH_2CH_2Ph$-), and the like. Further examples of aromatic radicals include 4-allyloxyphen-1-oxy, 4-aminophen-1-yl (i.e. $H_2NPh$-), 3-aminocarbonylphen-1-yl (i.e. $NH_2COPh$-), 4-benzoylphen-1-yl, dicyanoisopropylidenebis (4-phen-1-yloxy) (i.e. —$OPhC(CN)_2PhO$—), 3-methylphen-1-yl, methylenebis(phen-4-yloxy) (i.e. —$OPhCH_2PhO$—), 2-ethylphen-1-yl, phenylethenyl, 3-formyl-2-thienyl, 2-hexyl-5-furanyl; hexamethylene-1,6-bis(phen-4-yloxy) (i.e. —$OPh(CH_2)_6PhO$—); 4-hydroxymethylphen-1-yl (i.e. 4-$HOCH_2Ph$-), 4-mercaptomethylphen-1-yl (i.e. 4-$HSCH_2Ph$-), 4-methylthiophen-1-yl (i.e. 4-$CH_3SPh$-), 3-methoxyphen-1-yl, 2-methoxycarbonylphen-1-yloxy (e.g. methyl salicyl), 2-nitromethylphen-1-yl (i.e. —$PhCH_2NO_2$), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_8$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene2,2-bis (cyclohex-4-yl) (i.e. —$C_6H_{10}C(CF_3)_2C_6H_{10}$—), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}$—), and the like. Further examples of cycloaliphatic radicals include 4-allyloxycyclohex-1-yl, 4-aminocyclohex-1-yl (i.e. $H_2NC_6H_{10}$—), 4-aminocarbonyl-cyclopent-1-yl (i.e. $NH_2COC_5H_8$—), 4-acetyloxycyclohex-1-yl, 2,2-dicyanoisopropylidenebis(cyclohex-4-yloxy) (i.e. —$OC_6H_{10}C(CN)_2C_6H_{10}O$—), 3-methylcyclohex-1-yl, methylenebis(cyclohex-4-yloxy) (i.e. —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl; hexamethylene-1,6-bis(cyclohex-4-yloxy) (i.e. —OC$_6$H$_{10}$(CH$_2$)$_6$C$_6$H$_{10}$O—); 4-hydroxymethylcyclohex-1-yl (i.e. 4-HOCH$_2$C$_6$H$_{10}$—), 4-mercaptomethylcyclohex-1-yl (i.e. 4-HSCH$_2$C$_6$H$_{10}$—), 4-methylthiocyclohex-1-yl (i.e. 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (i.e. NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g. (CH$_3$O)$_3$SiCH$_2$CH$_2$C$_6$H$_{10}$—), 4-vinylcyclohexen-1-yl, vinylidenebis (cyclohexyl), and the like. The term "a C$_3$-C$_{10}$ cycloaliphatic radial" includes cycloaliphatic radicals containing at least three but no more than 10 carbon atoms. The cycloaliphatic radical 2-tetrahydrofuranyl (C$_4$H$_7$O—) represents a C$_4$ cycloaliphatic radical. The cyclohexylmethyl radical (C$_6$H$_{11}$CH$_2$—) represents a C cycloaliphatic radical.

The present invention relates to a method for preparing a purified dianhydride, said method comprising:

(a) preparing a first mixture comprising water, at least one inorganic acid, and at least one dianhydride;

(b) heating said first mixture until substantially all of said dianhydride is converted to a tetraacid comprised in a second mixture;

(c) filtering at least a portion of said second mixture to provide a solid tetraacid and a filtrate; and (d) heating the tetraacid provided by step (c) in a solvent with concurrent distillation of water to provide a third mixture comprising a purified dianhydride and a solvent.

Typically, the dianhydrides are selected from the group of dianhydrides represented by structure I

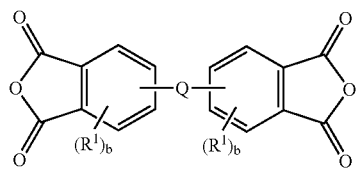

wherein R$^1$ is a halogen atom, a nitro group, a cyano group or hydrogen, a C$_1$-C$_{12}$ aliphatic radical, C$_3$-C$_{12}$ cycloaliphatic radical, or a C$_3$-C$_{12}$ aromatic radical; b is independently at each occurrence an integer from 0 to 3; Q is a bond, an oxygen atom, a sulfur atom, a sulfinyl group, a sulfonyl group, a selenium atom, a hexafluoroisopropylidene group, a C$_1$-C$_{30}$ aliphatic radical, a C$_3$-C$_{30}$ cycloaliphatic radical, or a C$_3$-C$_{30}$ aromatic radical, or a carbonyl group. In one embodiment Q is a linking group having structure II

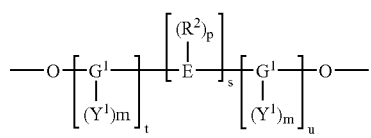

wherein each G$^1$ is independently an C$_3$-C$_{20}$ aromatic radical; E is selected from the group consisting of a C$_3$-C$_{20}$ cycloaliphatic radical, a C$_3$-C$_{20}$ aromatic radical, a C$_1$-C$_{20}$ aliphatic radical, a sulfur-containing linkage, a phosphorus-containing linkage, an ether linkage, a carbonyl group, a tertiary nitrogen atom, and a silicon-containing linkage; R$^2$ is independently at each occurrence a halogen atom, a C$_1$-C$_{20}$ aliphatic radical, C$_3$-C$_{20}$ cycloaliphatic radical, or a C$_3$-C$_{20}$ aromatic radical; Y$^1$ is independently at each occurrence a halogen atom, a nitro group, a cyano group, a C$_1$-C$_{20}$ aliphatic radical, C$_3$-C$_{20}$ cycloaliphatic radical, or a C$_3$-C$_{20}$ aromatic radical; each m is independently a number from zero through the number of positions on each respective G$^1$ available for substitution; p is a whole number from zero through the number of positions on E available for substitution; t is a number greater than or equal to one; s is either zero or one; and u is a whole number including zero. Suitable dianhydrides represented by formula I are illustrated by 4,4'biphenol dianhydride; 4,4'-oxydiphthalic anhydride; 4,4'-thiodiphthalic anhydride; sulfinyldiphthalic anhydride; sulfonyldiphthalic anhydride; 4,4'-selenyldiphthalic anhydride; 4,4'-(hexafluoroisiopropylidene) diphthalic anhydride (CAS No. 1102-00-2); biphenyldianhydride; 4,4'-carbonyldiphthalic anhydride CAS No. 2421-28-5); hexafluoroisopropylidene bisphthalic anhydride; and 4,4'-(4,4'-isopropylidene diphenoxy)bis(phthalic anhydride) i.e. bisphenol A bisphthalic anhydride.

In a specific embodiment of the present invention, the dianhydrides used are 4,4'-oxydiphthalic anhydride (hereinafter sometimes referred to as "ODPA") (structure V) and 4,4'-(4,4'-isopropylidene diphenoxy)bis(phthalic anhydride) (hereinafter sometimes referred to as "BPADA") (structure VI). In alternate embodiments, minor amounts of the 3,3'-oxydiphthalic anhydride and 3,4'-oxydiphthalic anhydride may be present along with the 4,4'-oxydiphthalic anhydride.

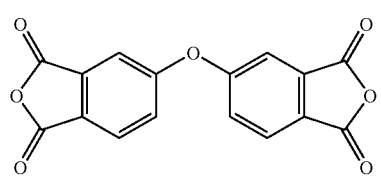

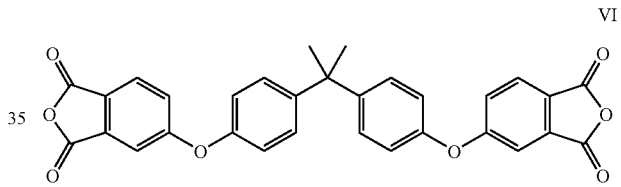

In one embodiment the dianhydride is selected from the group consisting essentially of 3,3'-oxydiphthalic anhydride and 3,4'-Oxydiphthalic anhydride.

The dianhydrides V and VI are commercially available or may be prepared by methods known to those skilled in the art. The dianhydride, 4,4' oxydiphthalic anhydride (structure V, CAS No. 1823-59-2) (ODPA) is a preferred dianhydride and is available commercially from Aldrich Chemical Co. The dianhydride, 4,4'-(4,4'-isopropylidene diphenoxy)bis(phthalic anhydride) (structure VI, CAS #38103-06-9) (BPADA) is a preferred dianhydride and is available commercially from Aldrich Chemical Co. In certain instances, BPADA may comprise a monofunctional contaminant. When present, it functions as a chain stopper and will affect the molecular weight of polymers prepared using BPADA under circumstances in which the BPADA comprises the monofunctional contaminant.

The dianhydride in one embodiment of the invention comprises at least impurity which is substantially soluble in aqueous acid. The at least one impurity is selected from the group consisting of ammonium salts, phosphonium salts and salts of inner transition metals. In a preferred embodiment said impurity is at least one compound selected from the group consisting of quaternary ammonium salts, quaternary phosphonium salts, and hexaalkyl salts of inner transition metals. The hexaalkyl salt is a hexaalkylguanidinium salt and more preferably a hexaethylguanidinium halide. In one embodiment the at least one impurity consists essentially of is hexaethylguanidinium chloride.

In one embodiment of the present invention the inorganic acid is at least one acid selected from the group consisting of boric acid, phosphoric acid, phosphorous acids, oxy acids of phosphorous, hydrochloric acid, hydrobromic acid, hydroiodic acid, sulfuric acid, sulfurous acid. For the purposes of this application, carbonic acid is defined as an inorganic acid. In a preferred embodiment the acid is at least one acid selected from the group consisting of carbonic acid and phosphoric acid. In one embodiment of the present invention the inorganic acid is added to the dianhydride followed by addition of water, to form a first mixture.

The first mixture may further comprise a diluent. The diluent is at least one selected from the group consisting of alcohols, ketones, amides, aromatic solvents and ethers. The diluent in a preferred embodiment is an alcohol. In another embodiment the diluent is at least one alcohol selected from the group consisting of lower alcohols like, methanol, ethanol, propanol and butanol. In yet another embodiment the diluent is orthodichlorobenzene (ODCB).

The preparation of purified dianhydride according to the method of the present invention comprises heating said first mixture substantially until all the dianhydride is converted to a tetraacid and forms a second mixture. The heating is carried out at a temperature in a range between about 30° C. and about 180° C., preferably between about 60° C. and about 160° C., and still more preferably between about 100° C. and about 130° C. Typically the heating is carried out at supraatmospheric pressure. The heating is carried out at a pressure in a range between about 1 bar and about 10 bar, preferably between about 3 bar and about 5 bar.

In one embodiment the dianhydride gets converted to its corresponding tetra acid. The tetraacid formed is of the structure VII

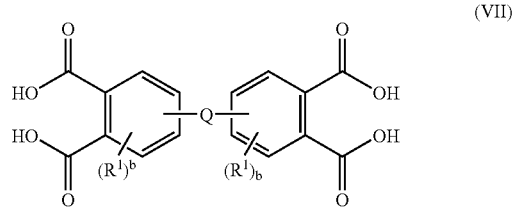

(VII)

wherein $R^1$ is a halogen atom, a nitro group, a cyano group or hydrogen, a $C_1$-$C_{12}$ aliphatic radical, $C_3$-$C_{12}$ cycloaliphatic radical, or a $C_3$-$C_{12}$ aromatic radical; b is independently at each occurrence an integer from 0 to 3; Q is a bond, an oxygen atom, a sulfur atom, a sulfinyl group, a sulfonyl group, a selenium atom, a hexafluoroisopropylidene group, a $C_1$-$C_{30}$ aliphatic radical, a $C_3$-$C_{30}$ cycloaliphatic radical, or a $C_3$-$C_{30}$ aromatic radical, or a carbonyl group. In one embodiment the oxydiphthalic dianhydride is converted to oxydiphthalic acid (hereinafter also known as "ODTA").

The tetraacid formed in the second mixture is filtered at room temperature and the solid tetraacid formed is isolated while the filtrate comprising at least a portion of said water soluble impurity. The filtration is carried by various methods known in the art. In one embodiment the filtrate was recycled for use in steps (a) and (b).

In one embodiment the solid tetraacid formed was heated in a solvent. Suitable solvents include non-polar solvents and polar aprotic solvents. Typically, the reaction is carried out in an aromatic solvent, for example an aromatic hydrocarbon solvent or chloroaromatic solvent. In one embodiment the solvent has a boiling point above about 120° C., preferably above about 150° C., and more preferably above about 180° C. Suitable solvents include, but are not limited to, toluene, xylene, orthodichlorobenzene (ODCB), para-dichlorobenzene, dichlorotoluene; 1,2,4-trichlorobenzene; diphenylether, dimethylsulfone, diphenyl sulfone, sulfolane, phenetole, anisole, veratrole, and mixtures thereof. In a preferred embodiment chlorinated aromatic liquids be employed as solvents, examples of which include, but are not limited to, ortho-dichlorobenzene (o-DCB); 2,4-dichlorotoluene; and 1,2,4-trichlorobenzene. In some embodiments 2,4-dichlorotoluene is a preferred solvent and in an alternate embodiment solvents, such as ortho-dichlorobenzene, is employed so that the reaction can be run at superatmospheric pressure to permit higher temperatures, higher reaction rates. In an alternate embodiment the heating with said solvent is carried out with constant concurrent distillation of water.

In one embodiment of the present invention the heating of the tetraacid with said solvent is carried out carried out at a temperature in a range between about 100-° C. and about 200° C., preferably between about 120° C. and about 190° C., and still more preferably between about 160° C. and about 180° C. The heating can carried out at atmospheric or supraatmospheric pressure. The heating is carried out at a pressure in a range between about 14 bar and about 28 bar, preferably between about 14 bar and about 20 bar. The heating is carried out for typically about 30 minutes to 800 minutes. Those skilled in the art can determine the time required for the heating to convert the tetraacid to the purified dianhydride or the progress could be monitored by chromatographic techniques. In one embodiment, the hydrolysis is carried out at supraatmospheric pressure at a temperature in excess of 100° C. This provides the advantages of a very rapid hydrolysis (<10 minutes) and in certain embodiments yields a homogeneous solution containing up to ~25 wt % solids. At this high solids level, loss of tetraacid to filtrate is minimized. For example, since ODTA is soluble at 0.5 wt % in water at room temperature. Thus, yields of ODTA as high as 100* 24.5/25=98% may be achieved.

EXAMPLES

The following examples are set forth to provide those of ordinary skill in the art with a detailed description of how the methods claimed herein are carried out and evaluated, and are not intended to limit the scope of what the inventors regard as their invention. Unless indicated otherwise, parts are by weight, temperature is in ° C.

The Method for ODPA Purification

EXAMPLES Ex. 1 to Ex. 7: A 250 mL round bottom flask was equipped with a condenser, a stir bar and was charged with 5 g oxydiphthalicacid anhydride (also known as "ODPA"; as an 83.8% solids wet-cake with residual orthodichlorobenzene, "ODCB") and 145 mL of HCl solution yielding a 2.79% solids slurry. The catalyst hexaethylguanidinium chloride (as known as "HEGCl") is present in the wet cake at a level of about 3500 ppm. The concentration of the HCl from Fisher Scientific was varied in the examples given in Table 1 by dilution to the appropriate concentration with deionized water (DI water). The flask was submerged into a 100° C. hot oil bath and the slurry was stirred for about one hour. ODPA slowly dissolved in the aqueous acid, as the corresponding ODTA is formed gradually. At the end of about 45 minutes all the ODPA was hydrolyzed leaving behind a clear solution. The temperature of the oil-bath was reduced; the solution was gradually cooled over a period of at least 3 hours. The final ODTA was filtered through a Buechner filter, washed with 50 mL of DI water, and then dried overnight in a vacuum oven at 120° C. The yield of ODTA was calculated and the amount of HEGCl and ODPA in the ODTA was established using NMR Spectroscopy.

TABLE 1

|  | Ex. 1 | Ex. 2 | Ex. 3 | Ex. 4 | Ex. 5 | Ex. 6 | Ex. 7 |
|---|---|---|---|---|---|---|---|
| Conc. HCl (N) | 0.10 | 1.0 | 1.0 | 0.1 (1st recycle) | 1.0 (1st recycle) | 0.1 (2nd recycle) | 1.0 (2nd recycle) |
| ODPA (g) | 5 | 5 | 5 | 5 | 5 | 5 | 5 |
| Initial HEGCl (ppm) | 3503 | 3503 | 3503 | 3503 | 3503 | 3503 | 3503 |
| % Solids | 83.8 | 83.8 | 83.8 | 83.8 | 83.8 | 83.8 | 83.8 |
| ODPA dry basis (g) | 4.2 | 4.2 | 4.2 | 4.2 | 4.2 | 4.2 | 4.2 |
| Acid Amount (mL) | 145 | 145 | 50 | 130 | 130 | 105 | 110 |
| Acid Recycle Information | Fresh | Fresh | Fresh | Filtrate of Ex. 1 | Filtrate of Ex. 2 | Filtrate of Ex. 4 | Filtrate of Ex. 5 |
| % Solids of Reaction Mixture | 2.79 | 2.79 | 7.62 | 3.10 | 3.10 | 3.81 | 3.64 |
| Crystallization Time (h) | 3 | 3 | 1.5 | 1.5 | Overnight | Overnight | Overnight |
| Water wash amount (mL) | 50 | 20 | 20 | 20 | 20 | 20 | 20 |
| ODTA Yield (theoretical) | 4.65 | 4.65 | 4.65 | 4.65 | 4.65 | 4.65 | 4.65 |
| Yield (g) | 3.16 | 3.65 | 3.94 | 4.16 | 4.45 | 4.57 | 4.06 |
| Yield (%) | 67.9 | 78.6 | 84.7 | 89.3 | 95.7 | 98.2 | 87.4 |
| Final HEGCl (ppm) | 1085 | 108 | 181 | 640 | 142 | 487 | 175 |

EXAMPLES Ex. 8 to Ex. 9: To a wet-cake of ODPA 1N HCl solution was added to yield a slurry of ODPA. The catalyst HEGCl is present in the wet cake at a level of about 3500 ppm. The slurry was hydrolyzed for about 3 to 5 hours at a temperature of about 100 to 150° C. and a pressure of about 78 psi. The ODTA formed was filtered through a Buechner filter, washed with ODTA saturated DI water (4 g per g of ODPA wetcake) or ODTA saturated DI water (1.6 g per g of ODPA wetcake) as shown in Table 2. The final yield was about 91% of ODTA and the amount of HEGCl present in the final product was established using HPLC Technique.

TABLE 2

|  | Ex. 8 | Ex. 9 |
|---|---|---|
| ODPA (g) | 3.7 | 80 |
| Initial HEGCl (ppm) | 2273 | 2273 |
| Acid Used | 1N HCl | ODTA saturated 1N HCl |
| Pressure (psi) | Atmospheric Pressure | 78 |
| Time (h) | 3 | 5 |
| Temperature (° C.) | 100 | 150 |
| % Solids of Reaction Mixture | 3.5 | 20 |
| Wash Solvent | ODTA saturated with DI water | ODTA saturated with DI water + 1N HCl |
| Amount of Wash Solvent (g) | 4.0 | 1.6 |
| Yield of ODTA (%) | 91 | 87 |
| Final HEGCl (ppm) | 133 | 152 |

EXAMPLES Ex. 10 to Ex. 21: The purification in these examples was carried out using similar method described in Table1. The acid used in these examples was phosphoric acid in varying concentrations. The experimental details are given in Table 3 and 4.

TABLE 3

|  | Ex. 10 | Ex. 11 | Ex. 12 | Ex. 13 |
|---|---|---|---|---|
| Phosphoric Acid (5% Aqueous) | $H_3PO_4$ | $H_3PO_4$ (1st recycle) | $H_3PO_4$ (2nd recycle) | $H_3PO_4$ |
| ODPA (g) | 5 | 5 | 5 | 5 |
| Initial HEGCl (ppm) | 3503 | 3503 | 3503 | 3503 |
| % Solids | 83.8 | 83.8 | 83.8 | 83.8 |
| ODPA dry basis (g) | 4.2 | 4.2 | 4.2 | 4.2 |
| Acid Amount (mL) | 160 | 150 | 130 | 50 |
| Acid Recycle Information | Fresh | Filtrate of Ex. 10 | Filtrate of Ex. 11 | Fresh |
| % Solids of Reaction Mixture | 2.55 | 2.72 | 3.12 | 7.73 |
| Crystallization Time (h) | 3 | Overnight | 3 | 2 |
| Water wash amount (mL) | 20 | 20 | 20 | 20 |
| ODTA Yield (theoretical) | 4.65 | 4.65 | 4.65 | 4.65 |
| Yield (g) | 3.67 | 4.57 | 3.87 | 3.68 |
| Yield (%) | 78.9 | 98.2 | 83.3 | 79.0 |
| Final HEGCl (ppm) | 109 | 325 | 20 | 56 |

TABLE 4

|  | Ex. 14 | Ex. 15 | Ex. 16 | Ex. 17 | Ex. 18 | Ex. 19 | Ex. 20 | Ex. 21 |
|---|---|---|---|---|---|---|---|---|
| Initial HEGCl (ppm) | 1258 | 1258 | 1258 | 1258 | 1677 | 1677 | 176 | 2273 |
| Acid Used | 5% aq. $H_3PO_4$ | Mother Liquor of Ex. 14 | 5% $H_3PO_4$ | Mother Liquor of Ex. 16 | Mother Liquor of Ex. 17 | 0.88 wt % $H_3PO_4$ in $H_2O$ | Mother Liquor of Ex. 19 | 3% aq. $H_3PO_4$ |
| Time (h) | 2 | 3 | 5 | 5 | 7.5 | 1 | 5 | 5 |
| % Solids of Reaction Mixture | 3.2 | 3.2 | 6.2 | 6.7 | 7.1 | 7.0 | 7.4 | 5.9 |

TABLE 4-continued

|  | Ex. 14 | Ex. 15 | Ex. 16 | Ex. 17 | Ex. 18 | Ex. 19 | Ex. 20 | Ex. 21 |
|---|---|---|---|---|---|---|---|---|
| Wash Solvent | 5% aq. $H_3PO_4$ | ODTA Saturated $H_2O$ | $H_2O$ | $H_2O$ | $H_2O$ | $H_2O$ | $H_2O$ | $H_2O$ |
| % wash solvent/g ODPA wet cake | 2.0 | 6.0 | 6.0 | 6.0 | 6.0 | 4.2 | 5.0 | 5.9 |
| Yield of ODTA (%) | 81 | 93 | 86 | 94 | 98 | 83 | 97 | 83 |
| Final HEGCl (ppm) | 91 | <75 | <75 | <75 | <10 | 176 | <60 | <71 |

EXAMPLES Ex. 22 and Ex. 25: A 1000 ml round bottom flask was charged with 120 grams of ODPA (87.4% solids wet cake with residual ODCB, and having HEGCl of about 3503 ppm) and 382.8 ml of a 3% (by weight) phosphoric acid solution which was spiked with 1000-10000 ppm of HEGCl. The spiking was carried out adding suitable amounts of about 15.8% HEGCl solution in ODCB. The flask was fitted with a nitrogen purge, an agitator and placed in an oil bath set at 105° C. with continuous stirring for 5 hours. The temperature was lowered to 25° C. and filtered in a Buechner funnel. The filtrate was washed with 600 ml. deionized water and subsequently dried overnight in a vacuum oven at 120° C. The filtrate about 95.81 g. was re-suspended in 1820.39 g. ODCB solution in 3-neck round bottom flask equipped with an agitator and a Dean-Stark's apparatus. A nitrogen sweep was maintained. The flask was heated to 200° C. in refluxing ODCB conditions to remove water by the use of the nitrogen sweep. The ODTA is initially formed as a slurry, but as the water was completely removed, ring closure of the filtrate to ODPA resulted leaving behind a clear solution. The removal of water required 48 fluid oz ODCB over a period of 6 hours. Subsequently, the reactor was allowed to cool to 25° C., leading to crystallization of ODPA. The cake was then dried in an oven at 120° C. under vacuum. The stirring time, acid used and temperature of the oil bath were varied as shown in Table 5.

TABLE 5

|  | Ex. 22 | Ex. 23 | Ex. 24 | Ex. 25 |
|---|---|---|---|---|
| Total Phosphoric Acid solution (g) | 16 | 16 | 16 | 16 |
| HEGCl in acid solution (ppm) | 1000 | 5000 | 10000 | 20000 |
| $H_3PO_4$ (g)/100 g acid solution | 3 | 3 | 3 | 3 |
| ODPA (g) | 5 | 5 | 5 | 5 |
| Initial HEGCl (ppm) | 3503 | 3503 | 3503 | 3503 |
| % Solids | 83.8 | 83.8 | 83.8 | 83.8 |
| % Solids of Reaction Mixture | 20 | 20 | 20 | 20 |
| Stirring Time (h) | 5 | 5 | 5 | 5 |
| Temperature (° C.) | 105 | 105 | 105 | 105 |
| ODPA dry basis (g) | 4.2 | 4.2 | 4.2 | 4.2 |
| Acid Amount (mL) | 160 | 150 | 130 | 50 |
| Crystallization Time (h) | 3 | 3 | 3 | 3 |
| Wash Fluid | Deionized water | | | |
| Water wash amount (mL) | 25 | 25 | 25 | 25 |
| Yield (g) | 4.3 | 4.3 | 4.3 | 4.3 |
| Yield based on total ODTA (%) | 91.7 | 92.2 | 92.6 | 91.7 |
| % Solids on wet-cake (%) | 65.7 | 67.7 | 67.8 | 57.3 |
| Final HEGCl (ppm) | 113 | 951 | 1814 | 3882 |

The Tables 6 and 7 show the alternate acids that were used instead of HCl or phosphoric acid. The purification was carried out in a similar manner to the one described for Example 1. The reaction conditions are described in Tables 6 and 7.

TABLE 6

|  | C. Ex. 1 | C. Ex. 2 | C. Ex. 3 | C. Ex. 4 | C. Ex. 5 |
|---|---|---|---|---|---|
| Acetic Acid (g)/100 g solution | 3.1 | 3.1 | 3.1 | 9.5 | 17.4 |
| Acid Amount (mL) | 160 | 155 | 140 | 130 | 130 |
| Acid Recycle Information | Fresh | Filtrate of C. Ex. 1 | Filtrate of C. Ex. 2 | Fresh | Fresh |
| ODPA (g) | 5 | 5 | 5 | 5 | 5 |
| Initial HEGCl (ppm) | 3503 | 3503 | 3503 | 3503 | 3503 |
| % Solids | 83.8 | 83.8 | 83.8 | 83.8 | 83.8 |
| ODPA dry basis (g) | 4.2 | 4.2 | 4.2 | 4.2 | 4.2 |
| Stirring Time (h) | 1 | 1 | 1 | 1 | 1 |
| % Solids of Reaction Mixture | 2.54 | 2.62 | 2.89 | 3.10 | 3.10 |
| Crystallization Time (h) | Overnight | 3 | 3 | Overnight | Overnight |
| Water wash amount (mL) | 20 | 20 | 20 | 20 | 20 |
| ODTA Yield (theoretical) | 4.65 | 4.65 | 4.65 | 4.65 | 4.65 |
| Yield (g) | 3.04 | 3.80 | 3.85 | 3.49 | 0 |
| Yield (%) | 65.4 | 81.6 | 82.7 | 75.0 | 0 |
| Final HEGCl (ppm) | 990 | 840 | 455 | 321 | Not recorded |

TABLE 7

|  | C. Ex. 6 | C. Ex. 7 | C. Ex. 8 | C. Ex. 9 |
| --- | --- | --- | --- | --- |
| Acid Used | ODTA saturated H₂O | 3% aq. Citric acid | EDTA saturated H₂O | 3% aq. Oxalic acid |
| Time (h) | 1 | 1 | 16 | 3 |
| Wash Solvent | H₂O | 3% aq. Citric acid | EDTA saturated H₂O | 3% aq. Oxalic acid |
| Wash Solvent (g)/ ODPA Wet-cake (g) | 6.0 | 4.0 | 4.0 | 4.0 |
| ODTA Yield (%) | 91 | 82 | 78 | 82 |
| Final HEGCl (ppm) | 916 | 1011 | 1028 | 1178 |

EDTA = ethylenediaminetetraacetic acid

The invention has been described in detail with particular reference to preferred embodiments thereof, but it will be understood by those skilled in the art that variations and modifications can be effected within the spirit and scope of the invention.

What is claimed is:

1. A method of purifying a dianhydride, said method comprising:
   (a) preparing a first mixture comprising water, at least one inorganic acid, and at least one dianhydride;
   (b) heating said first mixture until substantially all of said dianhydride is converted to a tetraacid comprised in a second mixture;
   (c) filtering at least a portion of said second mixture to provide a solid tetraacid and a filtrate; and
   (d) heating the tetraacid provided by step (c) in a solvent with concurrent distillation of water to provide a third mixture comprising a purified dianhydride and a solvent.

2. A method according to claim 1 wherein said first mixture further comprises a diluent selected from the group consisting of alcohols, ketones, amides, aromatic solvents, and ethers.

3. A method according to claim 2 wherein said diluent comprises orthodichlorobenzene.

4. A method according to claim 1 wherein said dianhydride is selected from the group consisting of dianhydrides having structure I

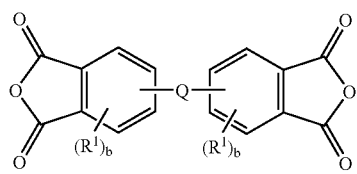

wherein Q is a bond, an oxygen atom, a sulfur atom, a sulfinyl group, a sulfonyl group, a selenium atom, a hexafluoroisopropylidene group, a $C_1$-$C_{30}$ aliphatic radical, a $C_3$-$C_{30}$ cycloaliphatic radical, or a $C_3$-$C_{30}$ aromatic radical, a carbonyl group; $R^1$ is a halogen atom, a nitro group, a cyano group or hydrogen, a $C_1$-$C_{12}$ aliphatic radical, $C_3$-$C_{12}$ cycloaliphatic radical, or a $C_3$-$C_{12}$ aromatic radical; b is independently at each occurrence an integer from 0 to 3.

5. A method according to claim 4 wherein said dianhydride is selected from the group consisting oxydiphthalic anhydride; thiodiphthalic anhydride; sulfinyldiphthalic anhydride; sulfonyldiphthalic anhydride; carbonyldiphthalic anhydride; bisphenol A bisphthalic anhydride, hexafluoroisopropylidene bisphthalic anhydride; and biphenyldianhydride.

6. A method according to claim 1 wherein the dianhydride contains a water-soluble impurity and said water-soluble impurity is selected from the group consisting of quaternary ammonium salts, quaternary phosphonium salts, hexalkylguanidinium salts, and mixtures thereof.

7. A method according to claim 6 wherein hexalkylguanidinium salt is hexaethylguanidinium chloride.

8. A method according to claim 1 wherein said inorganic acid comprises at least one acid selected from the group consisting of carbonic acid, boric acid, phosphoric acid, phosphorous acid, hydrochloric acid, sulfuric acid, sulfurous acid, hydrobromic acid.

9. A method according to claim 1 wherein said inorganic acid comprises at least one acid selected from the group consisting of carbonic acid, and phosphoric acid.

10. A method according to claim 1 wherein said inorganic acid consists essentially of carbonic acid.

11. A method according to claim 1 wherein said inorganic acid consists essentially of phosphoric acid.

12. A method according to claim 1 wherein said inorganic acid consists essentially of hydrochloric acid.

13. A method according to claim 1 wherein said heating comprises heating at a temperature in a range between about 60° C. and about 160° C.

14. A method according to claim 1 wherein said heating is carried out at supratmospheric pressure.

15. A method according to claim 1 wherein said solvent is orthodichlorobenzene.

16. A method of preparing a purified oxydiphthalic anhydride, said method comprising:
   (a) preparing a first mixture comprising water, at least one inorganic acid, and oxydiphthalic anhydride, said oxydiphthalic anhydride comprising at least one impurity which is soluble in aqueous acid;
   (b) heating said first mixture until substantially all of said anhydride is converted to 3, 3',4,4'-oxydiphthalic acid comprised in a second mixture;
   (c) filtering at least a portion of said second mixture to provide a solid 3, 3',4, 4'-oxydiphthalic acid and a filtrate; and
   (d) heating the 3, 3',4,4'-oxydiphthalic acid provided by step (c) in a solvent with concurrent distillation of water to provide a third mixture of a purified oxydiphthalic anhydride and a solvent.

17. A method according to claim 16 wherein said impurity is selected from the group consisting of quaternary ammonium salts, quaternary phosphonium salts, hexalkylguanidinium salts, and mixtures thereof.

18. A method according to claim 16 wherein said impurity is hexaethylguanidinium chloride.

19. A method according to claim 16 wherein said inorganic acid comprises at least one acid selected from the group consisting of carbonic acid, boric acid, phosphoric acid, phosphorous acid, hydrochloric acid, sulfuric acid, sulfurous acid, hydrobromic acid.

20. A method according to claim 16 wherein said solvent is orthodichlorobenzene.

21. A method of preparing a purified oxydiphthalic anhydride, said method comprising:
   (a) preparing a first mixture comprising water, phosphoric acid, and oxydiphthalic anhydride, said anhydride comprising at least one impurity, said impurity being soluble in aqueous acid;
   (b) heating said first mixture at temperature in a range between about 60° C. and about 160° C. and a pressure in a range between about 1 and about 4 atmospheres until substantially all of said anhydride is converted to 3, 3',4, 4'-oxydiphthalic acid comprised in a second mixture;
(c) filtering at least a portion of said second mixture to provide a solid 3, 3',4, 4'-oxydiphthalic acid and a filtrate, said filtrate comprising at least a portion of said impurity; and heating the 3, 3',4,4'-oxydiphthalic acid provided by step (c) in orthodichlorobenzene with concurrent distillation of water to provide a third mixture comprising a purified oxydiphthalic anhydride and orthodichlorobenzene.

* * * * *